United States Patent [19]

Yan

[11] Patent Number: 5,248,488
[45] Date of Patent: Sep. 28, 1993

[54] NATURAL GAS TREATING SYSTEM

[75] Inventor: Tsoung Y. Yan, Philadelphia, Pa.

[73] Assignee: Mobil Oil Corporation, Fairfax, Va.

[21] Appl. No.: 808,793

[22] Filed: Dec. 12, 1991

[51] Int. Cl.$^5$ .............................................. B01D 53/34
[52] U.S. Cl. ................................. 423/210; 423/226;
423/228; 423/229; 423/245.1; 585/822; 95/902;
95/117; 95/141
[58] Field of Search .................... 423/245.1, 210, 228,
423/242.2, 229; 208/252, 254; 585/822, 823,
860; 55/35, 75

[56] References Cited

U.S. PATENT DOCUMENTS

| | | | |
|---|---|---|---|
| 3,078,634 | 2/1963 | Milton | 55/75 |
| 3,354,078 | 11/1967 | Miale et al. | 585/374 |
| 4,044,098 | 8/1977 | Miller et al. | 423/210 |
| 4,094,777 | 6/1978 | Sugier et al. | 210/32 |
| 4,130,484 | 12/1978 | Marwil et al. | 55/70 |
| 4,385,994 | 5/1983 | Wilson et al. | 210/689 |
| 4,499,059 | 2/1985 | Jones et al. | 423/226 |
| 4,711,970 | 12/1987 | Chang et al. | 585/415 |
| 4,717,553 | 1/1988 | Turk | 423/245.1 |
| 4,795,482 | 1/1989 | Gioffre et al. | 423/245.1 |
| 4,814,152 | 3/1989 | Yan | 423/556.1 |
| 4,892,567 | 1/1990 | Yan | 55/33 |
| 4,895,708 | 1/1990 | Yan | 423/210 |
| 4,982,050 | 1/1991 | Gammie et al. | 423/210 |
| 5,053,209 | 11/1991 | Yan | 423/210 |
| 5,120,515 | 6/1992 | Audeh et al. | 423/230 |
| 5,141,724 | 8/1992 | Audeh et al. | 423/210 |

FOREIGN PATENT DOCUMENTS 2310795 10/1976 France .

Primary Examiner—Gary P. Straub
Assistant Examiner—Peter T. DiMauro
Attorney, Agent, or Firm—Alexander J. McKillop;
Dennis P. Santini; Laurence P. Hobbes

[57] ABSTRACT

A method for removing mercury from natural gas comprises addition of a sulfur-containing agent to form sulfides of mercury, addition of organic base to absorb hydrogen sulfide, and subsequent contact of said natural gas with a molecular sieve to remove water therefrom, further comprising contacting said organic base-containing natural gas with a guard bed to substantially remove said organic base prior to said removing of water.

20 Claims, 1 Drawing Sheet

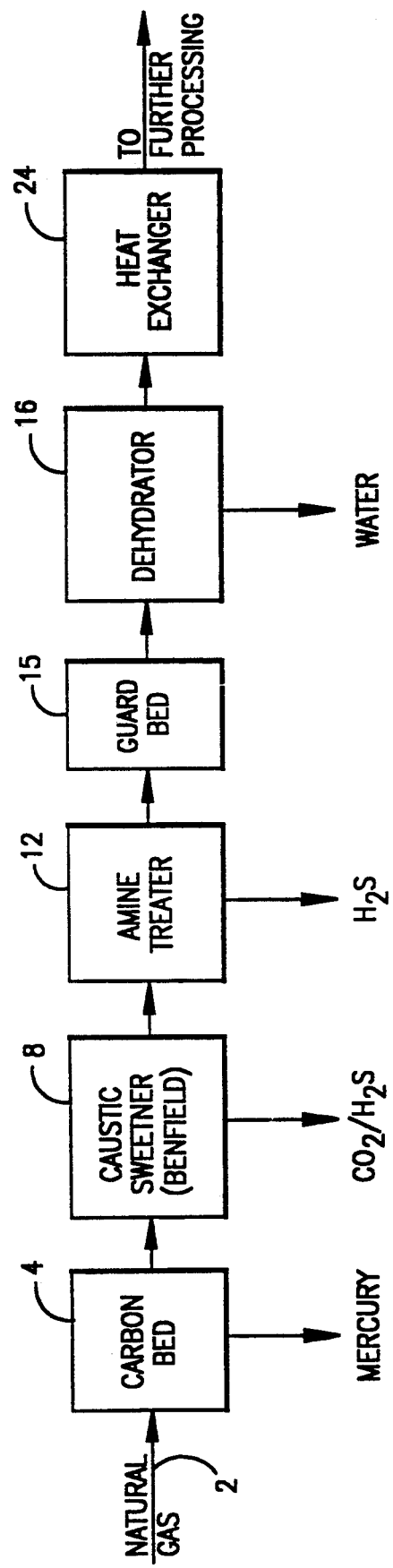

NATURAL GAS TREATING SYSTEM

BACKGROUND OF THE INVENTION

This invention relates to the purification of natural gas. More specifically, this invention relates to a method and system for removing sulfur compounds and water present in natural gas.

Raw natural gas must be treated prior to its liquefaction for several reasons. These include removing compounds which interfere with the liquefaction process, with the separation and recovery of hydrocarbon liquids and with meeting the specifications set for the recovered products. For example, the gas must be dried to prevent ice formation during cryogenic operations. Hydrogen sulfide ordinarily must be removed because of its toxic nature. A large number of commercial processes are in use for treating and separating of raw wellhead gas. The steps used in these different processes are each well known to those skilled in the art.

In addition, some natural gas contains mercury at levels as high as 200 to 300 micrograms per cubic meter. For example, the mercury level of natural gas produced from one field is reported in the literature to range from 200 to 330 micrograms per cubic meter. In another field the concentration was reported to range between 15 and 450 micrograms per cubic meter.

The processing of natural gas in LNG plants requires, at some location in the system, contact with equipment made primarily of aluminum. This is particularly true in the stage of processing where the gas has been treated by caustic or carbonate washing to remove $CO_2$ and $H_2S$ and then to treatment with liquid amine to complete $H_2S$ removal. One of the next steps is to chill or cool the gas in aluminum-constructed heat exchangers. Because large volumes of gas must be flowed through the aluminum heat exchangers, they are of a massive size and can represent a capital investment of several million dollars. Damage to these exchangers is to be avoided, if at all possible. One threat of damage comes from the mercury present in the gas flowing through the heat exchangers. Although the concentration of mercury appears low, its effect is cumulative as it amalgamates with the aluminum. The result is damage to the system, such as corrosion and stress cracking, which can lead to equipment failure, fires, and similar catastrophe. Repair of the aluminum heat exchangers damaged by mercury is almost impossible. Replacement of the heat exchangers represents a large expenditure. The down-time results in loss of product production. The problem of mercury in natural gas is discussed further in U.S. Pat. No. 4,094,777 and French Patent 2,310,795, both of which are incorporated herein by reference.

One method for removing mercury utilizes the addition of sulfurous materials, e.g., $H_2S$, to precipitate sulfides of mercury from the gas stream. U.S. Pat. No. 4,044,098 to Miller et al., incorporated herein by reference, teaches such a method which further utilizes treatment with organic base (amine) to absorb excess hydrogen sulfide to produce a gas stream of minimal sulfur content with a reduced mercury content. The product of such amine treatment can be passed through a dehydrator which comprises a zeolitic bed. One of the next steps is to chill or cool the gas in heat exchangers and to other additional equipment needed for further processing of the gas.

The zeolitic bed employed in the dehydrator can be damaged by carry-over of the organic base used in $H_2S$ removal. Organic bases, e.g., alkanolamines, can deposit carbon and destroy the structure and crystallinity of the molecular sieve and render it useless for drying. The resulting shortened life of the zeolitic bed requires unacceptably frequent replacement of the zeolitic bed as well as increased down time for the natural gas processing unit. Accordingly, it would be desirable to extend the service life of the zeolitic bed employed in the dehydrator by reducing carry-over of the organic base to the zeolitic bed.

SUMMARY OF THE INVENTION

Accordingly, one object of this invention is to remove the mercury present in natural gas to a concentration sufficiently low to avoid mercury damage to liquefaction equipment, such as aluminum heat exchangers, in a liquefied natural gas plant, while extending the life of molecular sieve dessicant used to remove water from the treated gas stream.

Still another objective is to provide a process for preventing or reducing organic base carry-over into molecular sieve dessicants which are employed to subsequently dry the treated gas stream wherein organic base is used to remove unreacted sulfur compounds which are added to remove mercury by precipitation to mercury sulfides.

The present invention relates to a method for separating mercury and water from natural gas comprising addition of a sulfur-containing agent to react with said mercury to form precipitated sulfides of mercury, addition of organic base to absorb unreacted sulfur-containing agent, and subsequent contacting of said natural gas with a molecular sieve dessicant to remove water therefrom, further comprising contacting said organic base-containing natural gas with an organic base absorbing guard bed to substantially remove said organic base prior to said removing of water.

The sulfur-containing agent can be added in the form of hydrogen sulfide or by contacting the natural gas with a substrate, e.g., activated carbon, impregnated with sulfur or sulfur compounds.

The organic bases are preferably introduced in solution such as alkanolamines, like monoethanolamine, diethanolamine, triethanolamine, methyldiethanolamine, alkanoldiamines, alkenylpolyamines, or solutions of salts of weak organic acids, such as amino carboxylic acids and aminosulfonic acids, or other alkaline liquids. Alkanolamines are especially preferred.

Molecular sieve dessicant used to dry the natural gas before passing to the heat exchanger can have an effective pore size ranging from 3 to 10 angstroms, preferably from 3 to 5 angstroms. Such zeolites include Zeolite A (3A, 4A and 5A), mordenite, and clinoptilolite. Particularly preferred molecular sieves can be selected from the group consisting of Zeolite 3A, Zeolite 4A, and Zeolite 5A, with Zeolite 5A (NaA), especially preferred.

The guard bed can comprise any suitable organic base-absorbing material. These materials should have the following properties: 1) high adsorption capacity, i.e., porous and high surface area; 2) high selectivity for organic base, e.g., amines, over moisture; 3) structures stable to organic base attack; and 4) regenerability at typical drier regeneration conditions, e.g., 650° F.

Suitable guard bed materials include activated charcoal, or a siliceous material. Such siliceous materials include those selected from the group consisting of clay, silica, silica gel, silica-alumina, and zeolite. The zeolites can include those selected from the group consisting of ZSM-5, ZSM-11, ZSM-22, ZSM-23, ZSM-35, ZSM-48, mordenite, clinoptilonite, erionite, and Zeolite Y. The organic base-adsorbing material, e.g. siliceous material, is preferably of high adsorption capacity as exhibited by a surface area of 1 to 1000 m$^2$ per gram, preferably 10 to 500 m$^2$ per gram. Another approach entails the use of an adsorbent of slight acidity, a strong acidity being undesirable owing to the difficult regeneration of strongly sorbed organic bases. The zeolites can be partially ion-exchanged and in the hydrogen form to adjust their acidity. As measured by alpha test, the organic base-adsorbing material, e.g., siliceous material, has an Alpha Value of 0.001 to 10, preferably an Alpha Value of 0.01 to 2.

Alpha Value is an approximate indication of the catalytic cracking activity of the catalyst compared to a standard silica-alumina cracking catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$) The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

The other group of useful sorbent is aluminum phosphates. Depending on the availability of proton in the compounds, i.e., $Al_2O_3/P_2O_5$ ratio, the acidities of the aluminum decrease in the following order: $Al(H_2PO_4)_3$, $Al_2(HPO_4)_3$, $ALPO_4$, $AL(PO_3)_3$. Thus, the composition of the aluminum phosphate mixture can be varied to meet the required acidity. The preferred mixture will have the Al/P atomic ratio of 0.6 to 1.

The structure of the aluminum phosphates and its mixtures can be either crystalline or amorphous. As a result, the aluminum phosphates can be synthesized hydrothermally or by mixing the desired amount of $H_3PO_4$ with alumina powder and steaming it at 100° to 400° C., preferably 200° to 300° C., for 1 to 2 hours.

The guard bed is placed upstream of the molecular sieve dessicant. In a preferred embodiment, the guard bed is simply placed on top of the molecular sieve dessicant and selectively intercepts the organic base, e.g., amine, present in the feedstream prior to its reaching the dessicant. To save valuable reactor volume, at least part of the guard bed adsorbent can be in bead or ball form and placed on the very top of the molecular sieve dessicant bed in lieu of conventional ceramic balls for stabilizing the bed. The guard bed comprises particles having at least $\frac{1}{8}$ cm diameter, preferably $\frac{1}{4}$ to 2 cubic inches. Cubic granules of 8 mesh to 2 in can be used in lieu of beads or balls.

The amount of guard material required depends on the concentration of organic base impurities in the gas and the competitive adsorption capacity of the guard material. We find that the volume ratio of the guard bed material to molecular sieve dessicant depends on the nature of the guard bed materials and the concentration of the amines entrained in the feed gas and ranges from 0.001 to 0.1, preferably 0.005 to 0.05.

The amines adsorbed on the guard bed material is stripped off simultaneously during the regeneration of the wet molecular sieve dessicant using hot gases. Thus, the guard bed material is regenerated along with the molecular sieve in one operation and is ready for the next cycle operation.

In accordance with this invention a process for treating a natural gas stream containing mercury is provided. The process entails flowing a natural gas feed containing mercury through a series of treating steps designed to remove mercury, hydrogen sulfide, and/or other sulfur-containing materials used to precipitate said mercury, as well as removing excess organic bases which are used to absorb the sulfur-containing materials prior to drying the feed by means of a molecular sieve dessicant. The treated gas then can be passed on to a heat exchanger and other liquefaction steps.

BRIEF DESCRIPTION OF THE DRAWING

The FIGURE is a schematic illustration of a system for treating natural gas in accordance with the invention; and

DETAILED DESCRIPTION OF THE INVENTION

As shown in the FIGURE, in one embodiment of the present invention, the natural gas 2 to be treated is first contacted in a treating bed 4 with an agent designed to remove the bulk of the mercury contamination. This treating zone can be a bed filled with a sorbent material such as silica, alumina, silica-alumina, or activated carbon having deposited on the surfaces thereof an active form of elemental sulfur or sulfur-containing material.

The gas in this section of the treating zone loses much of its mercury content by virtue of the reaction between the mercury and the sulfur to form mercuric sulfide. The effluent gas therefrom can then be carried through conventional Benfield and amine-treating units 8 and 12 to remove carbon dioxide and sulfides present in the gas. The effluent gas from this portion of the treatment which contains amine, generally in a form of entrainment, is then flowed into a guard bed 15 wherein said amine is absorbed and thence to dehydrator 16 where the moisture content of the gas is reduced to a desired level.

To save equipment and operation costs, the guard bed can be combined with the drier itself by placing the guard bed material on the top of the drier bed.

EXAMPLE 1

The amine adsorption capacity of the guard bed material is tested as follows:

Nitrogen gas is passed through a bath of aqueous solution containing 25% of DEA (diethanolamine) at 100° F. The effluent is then passed through beds of the guard bed materials for 24 hours to saturate the beds with the moisture and DEA. The DEA contents of the beds are:

| Material | DEA Adsorption, % of sorbent |
|---|---|
| Aluminum phosphate, Al/P = 0.8 | 8 |
| HZSM-5 Zeolite, Si/Al = 100 | 3 |
| Active carbon | 2 |

EXAMPLE 2

The saturated guard bed materials are regenerated by passing $N_2$ gas at 650° F. for 3 hours to simulate the drier bed regeneration condition. The regenerated guard bed material is used for adsorption testing as in Example 1. The adsorption capacities are the same as the first adsorption shown in Example 1.

The mercury-depleted dry gas is chilled in heat exchanger 24 and then conducted to further processing. The gas flowing to the liquefaction process is a gas substantially reduced in mercury content. The problems associated with mercury on aluminum, brass or copper surfaces present in the liquefaction portion of the system are accordingly alleviated.

What is claimed is:

1. In a method for separating mercury and water from natural gas comprising addition of a sulfur-containing agent to react with said mercury to form precipitated sulfides of mercury, addition of organic base to absorb unreacted sulfur-containing agent and to produce a mercury and sulfur depleted natural gas containing residual amounts of organic base, and subsequent contacting of said natural gas with a zeolite molecular sieve dessicant having an effective pore size ranging from 3 to 5 angstroms thereby removing water therefrom, the improvement further comprising contacting said organic base-containing natural gas with an organic base absorbing guard bed to remove essentially all said residual organic base prior to said removing water, wherein said guard bed comprises material selected from the group consisting of activated charcoal, amorphous aluminum phosphate, crystalline aluminum phosphate, clay, silica, silica-alumina, ZSM-5, ZSM-11, ZSM-22, ZSM-23, ZSM-35, ZSM-48, mordenite, clinoptilonite, erionite, and Zeolite Y, thereby reducing damage to the zeolite by carryover of organic base as compared to the non-use of the guard bed.

2. The method of claim 1 wherein said sulfur-containing agent comprises hydrogen sulfide.

3. The method of claim 1 wherein said organic base comprises amine.

4. The method of claim 3 wherein said amine is alkanol amine.

5. The method of claim 4 wherein said amine is selected from the group consisting of diethanolamine, monoethanolamine, triethanolamine, and methyldiethanolamine.

6. The method of claim 1 wherein said molecular sieve dessicant is selected from the group consisting of Zeolite 3A, Zeolite 4A, and Zeolite 5A.

7. The method of claim 6 wherein said molecular sieve dessicant is Zeolite 4A.

8. The method of claim 1 wherein said guard bed is selected from the group consisting of activated charcoal, amorphous aluminum phosphate, and crystalline alumina phosphate.

9. The method of claim 1 wherein said guard bed comprises activated charcoal.

10. The method of claim 1 wherein said guard bed comprises material selected from the group consisting of clay, silica, silica-alumina, ZSM-5, ZSM-11, ZSM-22, ZSM-23, ZSM-35, ZSM-48, mordenite, clinoptilonite, erionite, and Zeolite Y.

11. The method of claim 10 wherein said guard bed comprises material selected from the group consisting of ZSM-5, ZSM-11, ZSM-22, ZSM-23, ZSM-35, ZSM-48, mordenite, clinoptilonite, erionite, and Zeolite Y.

12. The method of claim 1 wherein said guard bed comprises aluminum phosphate having an Al/P atomic ratio of 0.6 to 1.

13. The method of claim 9 wherein said guard bed has a surface area of 1 to 1000 $m^2$ per gram.

14. The method of claim 13 wherein said guard bed has a surface area of 10 to 500 $m^2$ per gram.

15. The method of claim 10 wherein said guard bed material has an alpha value of 0.001 to 10.

16. The method of claim 15 wherein said guard bed material has an alpha value of 0.01 to 2.

17. The method of claim 1 wherein said guard bed is situated on top of said molecular sieve dessicant.

18. The method of claim 1 wherein said guard bed comprises particles having at least ⅛ inch diameter.

19. The method of claim 1 wherein the volumetric ratio of said guard bed to said molecular sieve dessicant ranges from 0.001 to 0.1.

20. The method of claim 3 wherein said amine is diethanolamine, said molecular sieve dessicant is Zeolite 4A, said guard bed comprises a siliceous material having an alpha value of 0.01 to 2 and comprising particles having at least ⅛ inch diameter, and the volumetric ratio of said guard bed to said molecular sieve dessicant ranges from 0.005 to 0.1.

* * * * *